(12) United States Patent
Pixton et al.

(10) Patent No.: US 9,655,511 B2
(45) Date of Patent: May 23, 2017

(54) APPARATUS AND METHOD TO OBTAIN CLINICAL OPHTHALMIC HIGH ORDER OPTICAL ABERRATIONS

(71) Applicant: Johnson & Johnson Vision Care, Inc., Jacksonville, FL (US)

(72) Inventors: Bruce M. Pixton, Woodbridge, VA (US); John E. Greivenkamp, Tucson, AZ (US); Gregory A. Williby, St. Johns, FL (US); Russell Spaulding, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 11 days.

(21) Appl. No.: 14/750,493

(22) Filed: Jun. 25, 2015

(65) Prior Publication Data

US 2015/0289759 A1   Oct. 15, 2015

Related U.S. Application Data

(62) Division of application No. 13/025,862, filed on Feb. 11, 2011, now Pat. No. 9,095,280.

(60) Provisional application No. 61/303,753, filed on Feb. 12, 2010.

(51) Int. Cl.
| | |
|---|---|
| *A61B 3/02* | (2006.01) |
| *A61B 3/032* | (2006.01) |
| *A61B 3/10* | (2006.01) |
| *A61B 3/00* | (2006.01) |
| *G02C 7/02* | (2006.01) |

(52) U.S. Cl.
CPC ............ *A61B 3/032* (2013.01); *A61B 3/0025* (2013.01); *A61B 3/1015* (2013.01); *G02C 7/027* (2013.01)

(58) Field of Classification Search
CPC ....... A61B 3/024; A61B 3/032; A61B 3/1015; A61B 3/103
USPC .................................... 351/222.246
See application file for complete search history.

(56) References Cited

U.S. PATENT DOCUMENTS

| | | | |
|---|---|---|---|
| 4,495,313 | A | 1/1985 | Larsen |
| 4,680,336 | A | 7/1987 | Larsen |
| 4,889,664 | A | 12/1989 | Kindt Larsen |
| 5,039,459 | A | 8/1991 | Kindt Larsen |
| 5,057,578 | A | 10/1991 | Spinelli |
| 5,314,960 | A | 5/1994 | Spinelli |

(Continued)

FOREIGN PATENT DOCUMENTS

| | | |
|---|---|---|
| CN | 101057170 A | 10/2007 |
| DE | 102007032001 | 1/2009 |

(Continued)

OTHER PUBLICATIONS

Palusinski I A et al: "Lateral-Shift Variable Aberration Generators", Applied Optics, Optical Society of America, US, vol. 38, No. 1, Jan. 1, 1999 (Jan. 1, 1999), pp. 86-90, XP000791919, ISSN: 0003-6935, DOI: D0I:10.1364/AO.38.000086.

(Continued)

*Primary Examiner* — James Greece

(57) ABSTRACT

An apparatus and method to improve the prescribing of customized ophthalmic corrections which contain higher order aberration. The apparatus enables the subjective measurement of higher order aberrations such as spherical aberration which can be used as part of the prescription for customized ophthalmic corrections.

1 Claim, 12 Drawing Sheets

(56) References Cited

U.S. PATENT DOCUMENTS

| | | |
|---|---|---|
| 5,371,147 A | 12/1994 | Spinelli |
| 5,540,410 A | 7/1996 | Lust |
| 6,880,933 B2 | 4/2005 | Davis |
| 7,517,087 B2 | 4/2009 | Dick |
| 7,744,217 B2 | 6/2010 | Cabeza |
| 7,753,521 B2 | 7/2010 | Wooley |
| 2003/0011783 A1 | 1/2003 | Suzuki |
| 2003/0081174 A1 | 5/2003 | Ross |
| 2004/0100617 A1 | 5/2004 | Abitbol |
| 2004/0263786 A1* | 12/2004 | Williams et al. ............. 351/246 |
| 2005/0225750 A1 | 10/2005 | Dick |
| 2005/0280777 A1 | 12/2005 | Dai |
| 2007/0109497 A1 | 5/2007 | Chang |
| 2007/0279586 A1* | 12/2007 | Jethmalani et al. .......... 351/164 |
| 2008/0018855 A1 | 1/2008 | Larichev |
| 2008/0137035 A1 | 6/2008 | Dick |
| 2009/0015787 A1 | 1/2009 | Guillen |

FOREIGN PATENT DOCUMENTS

| | | | |
|---|---|---|---|
| EP | 1486160 A2 | 12/2004 | |
| EP | 1486160 A3 | 3/2005 | |
| EP | 1486160 B1 | 12/2008 | |
| JP | 2001507258 A | 6/2001 | |
| JP | 2005506866 A | 3/2005 | |
| JP | 2005200823 A | 7/2005 | |
| JP | 2008503271 A | 2/2008 | |
| TW | 529927 B | 5/2003 | |
| TW | 200720698 A | 6/2007 | |
| TW | 201005348 A | 2/2010 | |
| WO | 9827863 A1 | 7/1998 | |
| WO | WO0209579 A1 | 2/2002 | |
| WO | WO03034909 A2 | 5/2003 | |
| WO | WO2006054985 A1 | 5/2006 | |
| WO | WO2009007368 A1 | 1/2009 | |

OTHER PUBLICATIONS

Lopez-Gil et al: "Generation of third-order spherical and coma aberrations by use of radially symmetrical fourth-order lenses", Journal of the Optical Society of America A, Optical Society of America, US, vol. 15, No. 9, Sep. 1, 1998 (Sep. 1, 1998), pp. 2563-2571, XP002138673, ISSN: 1084-7529.

Bruce M. Pixton: "Spherical Aberration Gauge for the Human Visual System", A Dissertation Submitted to the Faculty of the College of Optical Sciences, Jul. 29 2009, pp. 1-155.

* cited by examiner

APPARATUS AND METHOD TO OBTAIN CLINICAL OPHTHALMIC HIGH ORDER OPTICAL ABERRATIONS

CROSS REFERENCE TO RELATED APPLICATION

This application is a divisional application of U.S. application Ser. No. 13/025,862 filed on Feb. 11, 2011 which claims the benefit of U.S. Provisional Application No. 61/303,753 filed on Feb. 12, 2010.

BACKGROUND OF THE INVENTION

This invention relates to the design and methods for improving the final prescription of customized ophthalmic corrections. Sphero-cylindrical corrections are well known, and have been used extensively. Customized corrections, however, can include not only conventional sphero-cylindrical correction, but also the correction of higher order aberrations such as spherical aberration that require more precise determination of the subjectively acceptable final prescription. Currently available aberration measurement devices only measure the objective aberration values and do not produce values of higher order aberrations that are optimal and subjectively acceptable for the design of a customized ophthalmic correction. This invention provides an apparatus and method to improve the prescribing of customized ophthalmic corrections including lenses or surgical profiles.

SUMMARY OF THE INVENTION

The invention is an apparatus which enables the determination of the acceptable subjective level of correction for a higher order aberration such as spherical aberration. The result can be used to design custom ophthalmic corrections including lenses or refractive surgical profiles incorporating sphero-cylindrical refractive error and higher order aberrations such as spherical aberration.

In a further aspect, the apparatus comprises a pair of mating polynomial plates, placed in the visual path, which introduces specific controlled amounts of aberrations.

In yet a further aspect of the invention, the aberration generator is located at the stop of a 1× Keplerian telescope, so that efficient coupling is achieved between the pupil of the eye and the aberrations introduced by the generator.

In yet a further aspect of the invention, the aberration generator is achieved by the use of phase plates located at the pupil plane of an optical assembly.

In yet another aspect of the invention, ophthalmic trial lenses are introduced into the visual path at the pupil plane of the optical assembly.

In yet another aspect of the invention, a prism assembly or air-spaced mirror assembly is used in the aberration generator to erect the image produced by the optical assembly to preserve the orientation of the object viewed.

In yet another aspect of the invention, a periscope assembly consisting of two air-spaced mirrors is used so that the optical assembly line of sight and the subject's line of sight are co-incident.

In yet another aspect of the invention, an infrared light emitting diode (LED) illumination system is configured to illuminate the subject's pupil so that the apparatus may be aligned to the subject's line of sight.

In yet another aspect of the invention, a beam splitter is placed in front of the objective lenses of the optical assembly so that the alignment of the test subject's pupils to the telescope may be adjusted and tracked, as well as pupil size and test subject's line of sight.

In yet a further aspect of the invention, a method for designing and dispensing a customized ophthalmic correction includes obtaining a patient's low order objective sphero-cylindrical refractive prescription, subjective sphero-cylindrical refractive prescription, objective high order aberrations, subjective higher order aberrations such as spherical aberration, designing and fabricating a custom ophthalmic lens incorporating one or all of these measurements, and fitting the lens into, on or in front of a patient's eye.

In yet a further aspect of the invention, a method for designing and dispensing a customized ophthalmic correction includes obtaining a patient's low order objective sphero-cylindrical refractive prescription, subjective sphero-cylindrical refractive prescription, objective high order aberrations, subjective higher order aberrations such as spherical aberration, designing a custom surgical profile, and applying this correction to the eye by suitable means.

In yet another aspect of the invention, a method to generate an ophthalmic correction includes the steps of obtaining low order spherocylindrical refraction data, subjective higher order refraction data, and generating an ophthalmic correction.

In yet another aspect of the invention, individual subjective higher order aberration data is considered for the high order portion.

In yet another aspect of the invention, the individual subjective higher order aberration data is an average of multiple files.

In yet another aspect of the invention, large population subjective higher order aberration data is considered for the high order portion.

In yet another aspect of the invention, the subjective aberration is rotationally symmetric.

In yet another aspect of the invention, the subjective aberration is spherical aberration In yet another aspect of the invention, the subjective aberration is non-rotationally symmetric.

In yet another aspect of the invention, the subjective aberration is coma

In yet another aspect of the invention, the subjective aberration is trefoil.

In yet another aspect of the invention, the subjective aberration is obtained using a continuous aberration generator.

In yet another aspect of the invention, sub population subjective higher order aberration data is considered for the high order portion.

In yet another aspect of the invention, data is collected to describe the level, range, resolution and tolerance of a subjective higher order ophthalmic correction.

In yet another aspect of the invention, methods of designing ophthalmic corrections incorporating the subjective correction of higher order aberrations are encoded into instructions such as machine instructions and are programmed into a computer.

BRIEF DESCRIPTION OF THE DRAWINGS

FIG. 4 Shows a test eye chart.

DETAILED DESCRIPTION

Figure 1:
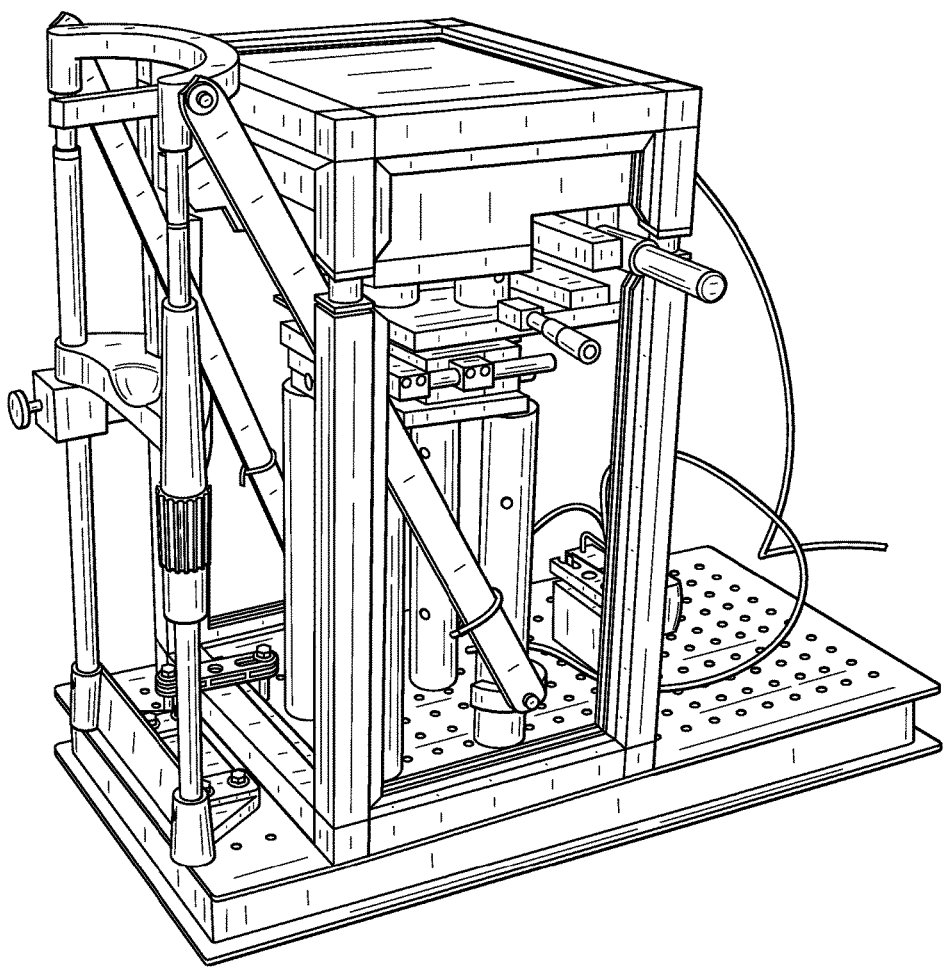
FIG. 1 is a depiction of an apparatus used to determine subjective values of higher order aberrations.

The invention is an apparatus useful in refining the design of customized ophthalmic correction including ophthalmic lenses, methods for using and prescribing these lenses, and by refractive surgery. By ophthalmic lenses is meant contact lenses, spectacle lenses, intraocular lenses, and inlay or onlay lenses. Preferably, ophthalmic lenses are contact lenses. Preferably, the ophthalmic lens is a customized contact lens which incorporates subjectively optimized values for higher order aberrations. By refractive surgery is meant Lasik, Lasek, PRK and the like.

By higher order aberrations is meant aberrations such as spherical aberration, coma, trefoil or other aberrations which are distinct from zero or first order aberrations such as spherical and astigmatic error. Preferably, higher order aberrations are spherical aberration.

By optical assembly or apparatus is meant an alignable binocular or monocular optical system capable of viewing a target at a specified distance including optical infinity or near, and introducing a controllable amount of higher order aberration.

Various measurements are used to provide data for vision correction and are incorporated into lens prescription and design. Conventional sphero-cylindrical refraction using a retinoscope, autorefractor such as the Nidek ARK-700A (Nidek Co., Ltd., Gamagori, Aichi, Japan) or the like yields the patient's low order sphero-cylindrical corrective prescription components. This is further refined subjectively using a phoropter such as the Nidek RT-5100 (Nidek Co., Ltd., Gamagori, Aichi, Japan) or the like, yielding the conventional low order values for spherical power, cylindrical power and cylinder axis. Higher order refractive correction is enabled by a wavefront measurement. Ocular wavefront data is collected from a patient using a wavefront sensor such as a COAS (Wavefront Sciences Inc., Albuquerque, N.M.). This wavefront data is generally in the form of Zernike polynomial coefficients, but can also be a set of wavefront heights at specified Cartesian or polar coordinates. A preferred system to designate the Zernike coefficients has been described as the OSA (Optical Society of America) method, in ANSI Z80.28 and is incorporated herein by reference.

The method to design ophthalmic corrections can be used for individuals on a custom lens basis or averaged for large populations, or sub-populations. Data obtained by this method can be collected to describe the level, range, resolution and tolerance of a subjective higher order ophthalmic correction. Obtaining the basic low order objective refractive prescription can be determined by the use of a retinoscope, autorefractor, or the like. Acquiring low order subjective refractive prescription can be determined by the use of a phoropter or the like. The objective higher order aberrations can be acquired by using a wavefront sensor or the like, while the subjective higher order refraction is acquired by the apparatus and method of this invention. The inventive methods of prescribing and providing customized ophthalmic corrections take into account the subjective acceptance of higher order refraction elements.

Spherical aberration is defined as follows. The measurement of the eye's spherical aberration has taken several different formats. The first format is derived from optical engineering in which aberrations are measured in waves or microns of departure from a reference. The second format is attributed to ophthalmic optics in which aberrations are considered a power error (or sometimes a power correction), measured in Diopters. Conversion of terms between the two communities is facilitated by the radially-dependent power error expression (Equation 1):

$$d\phi = \frac{1}{r}\frac{\partial W(r)}{\partial r}, \qquad (1)$$

where r is the unscaled pupil radius and W(r) is a radially-dependant wave aberration function. The wave aberration function representing spherical aberration can be written in terms of r as (Equation 2):

$$W(r) = W_{040}\left(\frac{r}{r_{max}}\right)^4, \qquad (2)$$

where $W_{040}$ is the wavefront expansion term for spherical aberration and $r_{max}$ is the maximum radial extent. By combining Equations (1) and (2) a relationship between the wave aberration and the power error expressions for Spherical Aberration can be determined (Equation 3):

$$d\phi_{SA} = \frac{4}{r_{max}^4}W_{040}r^2. \qquad (3)$$

It is sometimes further desirable to express spherical aberration as a quantity independent of the pupil radius. This is commonly done in ophthalmic optics by normalizing (Equation 4) the power error by $r_{max}^2$:

$$d\phi_{SA} = \frac{4}{r_{max}^4}W_{040} \qquad (4)$$

The units in Equation (4) are commonly reported as $mm^{-3}$ or $D/mm^2$. This relationship was used to convert the spherical aberration values obtained with the inventive apparatus into terms of power error, according to ophthalmic convention. Spherical aberration is thus defined in units of $D/mm^2$. Similar relationships between optical engineering descriptions and ophthalmic descriptions of other high order aberrations may be established in the same manner.

The optical assembly design includes the generation of continuously variable and controllable aberrations. Lateral-shift variable aberration plates were proposed by Palusinski, et al. [21]. This aberration generating technique is an extension of the variable-power lens proposed by Luis W. Alvarez [26] and which is today commonly known as the "Alvarez Lens". A pair of mating polynomial plates are placed in a beam path. By shifting the plates laterally and in opposite directions to each other, the relative shift acts like a differentiation operation on the wavefront passing through the plates. The polynomial surface solution that Alvarez found was third-order, which when shifted produced a second-order (defocus or power) wavefront. The general solution found by Palusinski, et al. describes the surfaces required to generate all of the third-order wavefront aberrations. For generation of spherical aberration, the appropriate polynomial surface profile T(x, y) is fifth-order and is given by Equation 5:

$$T(x, y) = k\left(\frac{1}{5}x^5 + \frac{2}{3}x^3y^2 + xy^4\right), \quad (5)$$

where k is a scaling factor. When shifted along x by equal and opposite amounts a and –a, the plates will generate a wavefront aberration W(x,y) given by Equation 6:

$$W(x, y) = 2ka(n-1)\left[(x^2 + y^2)^2 + 2a^2x^2 + \frac{2}{3}a^2y^2 + \frac{1}{5}a^4\right] \quad (6)$$

$$= \kappa a(x^2 + y^2)^2 + 2\kappa a^3(x^2 + y^2) - \frac{4}{3}\kappa a^3 y^2 + \frac{1}{5}\kappa a^5,$$

where $\kappa = 2k(n-1)$ is a constant for a given design. From Equation (6), it can be seen that while primarily producing the desired fourth-order or spherical aberration wavefront terms, additional second-order wavefront terms (corresponding to defocus and astigmatism) are also generated. These additional aberrations are considered parasitic to this method of aberration generation and cannot be eliminated entirely, although they can be attenuated below an acceptable threshold by the proper design of the system.

Two approaches can be used to minimize the generation of these parasitic aberrations and thus improve the quality of the generated spherical aberration wavefront. The first approach arises from a simple ratio evaluation of W(x,y), where the generated amounts of fourth-order aberration (spherical aberration) and second order aberrations (defocus and astigmatism) are compared in Equations (7) and (8):

$$\frac{W_{SA}}{W_{def}} = \frac{\kappa a(x^2 + y^2)^2}{2\kappa a^3(x^2 + y^2)} \quad (7)$$

$$= \frac{r^2}{2a^2}$$

and $$\frac{W_{SA}}{W_{asti}} = \frac{\kappa a(x^2 + y^2)^2}{\frac{4}{3}\kappa a^3 y^2} \quad (8)$$

$$= \begin{cases} \frac{3y^2}{4a^2}: x = 0 \\ \infty: y = 0, \end{cases}$$

where $r^2 = x^2 + y^2$ defines the radial extent of the wavefront aperture on the plates. From either Equation (7) or (8), the ratio comparison suggests that if the size of the aperture r is large in comparison to the shift amount a, then the amount of spherical aberration generated will be much more than the amount of parasitic aberrations generated. In fact, the ratio of r to a does not need to be very large before the proportional amount of generated parasitic aberrations show rapid decline, since it is the square of this ratio that is important.

A second approach to reducing parasitic aberration generation involves using some of the available cubic terms in the surface description T(x, y) to help balance the second-order wavefront aberrations. How much of each cubic term should be added is not clear by simply examining Equation 6. An analysis, however, has been performed by using the minimum variance attribute of Zernike polynomial terms, which can identify appropriate amounts of these cubic terms. In this analysis, the surface T(x, y) is first converted to an equivalent Zernike surface, and then all terms lower than fifth-order are removed. Since the generated wavefront is approximately the derivative of the surface description, the wavefront resulting from the surface terms that were removed would only have added positively to the overall wavefront variance. By removing the lower order Zernike terms from T(x, y), the resulting surfaces when shifted should generate a fourth-order wavefront with a minimum of the residual parasitic aberrations. Transforming the surface back to the original Polynomial form gives the below modified version of Equation (5), as Equation (9):

$$T(x, y) = k\left(\frac{1}{5}x^5 + \frac{2}{3}x^3y^2 + xy^4 - \frac{4}{15}x^3 - \frac{4}{5}xy^2 + \frac{1}{10}x\right). \quad (9)$$

It should be noted that the effect of the additional terms in Equation 9 is to minimize the influence of the parasitic aberrations across the full range of the lateral shift. If an asymmetric range of spherical aberration values is desired, or if the parasitic aberrations around the zero spherical aberration value need to be better controlled than those at the edge of the range, the cubic terms in Equation 9 should be altered accordingly.

Because this device is to be used for human vision, the range of spherical aberration correction values should represent the range of spherical aberration values observed in the population. Using the reported numbers from Porter, et al. for a study on 218 eyes, the average measured spherical aberration was about +0.14 μm of $Z_{4,0}$ for a 5.7 mm pupil. Converting this into the wavefront aberration term $W_{040}$ for a 6 mm pupil gives a population average of about +3.9 waves of spherical aberration at λ=594 nm. Error bars shown in the same study also suggest that individual variations can be as much as 3 waves on either side of the average. To provide a widely-accommodating range of variable spherical aberration correction for a general population, the apparatus should be designed to generate as much as 7 waves of negative spherical aberration to about 2 waves of positive spherical aberration.

Another continuous aberration generator involves two counter-rotating Zernike plates (Acosta and Bara, 2005). The use of these rotating plates is similar to the ideas already discussed, where two mating Zernike surfaces generate variable aberrations when rotated with respect to each other. The concept is attractive, since rotary motion is often easier to generate than lateral motion. A rotating plate design provides an alternate solution to the introduction of non-rotationally symmetric higher order aberrations into the vision system. In an alternate aspect, aberrations may be introduced into an optical assembly by other means including a spatial light modulator, Fresnel plate, adaptive optical device, deformable mirror, digital micro-mirror device and the like.

Some ophthalmic devices can be designed for good on-axis performance only, however this is not a useful design principle for visual devices where it desired to allow the eye to view its environment in a natural way. To design a spherical aberration corrector for operation over a moderate visual field)(±4°, the wavefront correction should be mapped directly into the pupil of the eye. This condition eliminates the appearance of off-axis wavefront errors. This mapping to the pupil of the eye has been acknowledged as important for any high-order aberration correction over a moderate field.

One of the simplest ways to map a spherical aberration correction into the pupil of the eye is to place the aberration generator at the aperture stop of an optical assembly such as a 1× Keplerian telescope, with the eye placed at the real exit pupil of the telescope. With the aberration generator at the stop, the bundle of rays will pass through the center of the generator for all field angles. This telescope is designed to work over a ±4° Field of View. The various fields converge nicely at the exit pupil. By having a real exit pupil that is external to the telescope, a 1× Keplerian allows efficient coupling between the pupil of the eye and the mapped aberration correction. In an alternate embodiment, an optical relay system other than a Keplerian telescope may be used.

Modifications to this basic design can be made for improving the overall system performance. Achromatization of the telescope and reduction of wavefront aberrations can be handled by appropriate lens design techniques, using the multiple surfaces of the telescope as design parameters and considering the optical path through the aberration generating plates. Additionally, because the image produced by a Keplerian telescope is inverted, proper erection of the image is required if the Gauge is to preserve orientation of the object in view. This is typically handled by a prism assembly in the design of a standard pair of binoculars, but can be treated equally as well by using air-spaced mirrors. The four reflections in the image erection system are usually accompanied by a deviation in the line of sight and possibly a change in the interpupillary distance. Because the Gauge was designed to preserve the subject's view as completely as possible, two additional mirrors in periscope configuration were used to bring the telescope line of sight coincident with the subject's line of sight.

Pupil size is also relevant to the present invention. Natural pupils were used for the examples provided herein, requiring that the illumination be maintained at a consistent level. The pupils were not dilated as a result of the administration of any medication. A low light setting for the spherical aberration measurements was determined to be best, as the effects of spherical aberration increase with the larger pupil sizes induced by lower light levels. The illumination at the vision targets was kept at about 48 lux. The viewing target illuminance values at this light level were slightly different for the two targets because of the dominant white space in the eye chart. After light transmission losses through the inventive apparatus of about 50%, the effective illuminances at the eye were 5.6 $cd/m^2$ and 3.3 $cd/m^2$ for the eye chart and the photo scene, respectively. When the Shack-Hartmann wavefront aberrometer device was in use, the lighting was adjusted accordingly, so that similar illumination conditions were observed for the objective measurements as well.

While the natural pupil sizes under these conditions ranged from 5 mm to 8 mm, any comparison of spherical aberration needed to be made at a common pupil diameter. The spherical aberration values were calibrated over a 6 mm pupil, and since these calibration values were the same for everyone tested, no further conversion for pupil size was needed. Since the Shack-Hartmann measurements provided objective measurements on spherical aberration that would be useful for comparison, these data sets were also scaled accordingly to fit a 6 mm pupil.

Optionally, data regarding the topography of the cornea is collected from a patient using a device such as the Keratron or Keratron Scout, (Optikon 2000, Rome, Italy). These devices function by interpreting the reflection of multiple annular ring images off of the cornea. The topographic data is available in several formats. The preferred format in the present invention is to depict the cornea as a topographic elevation map. The topography data may be utilized in customizing a contact lens design by using such data to guide selection of the most appropriate back surface contact lens shape. The topography data is also useful for understanding whether the source of ocular aberrations is corneal or internal to the eye.

In a preferred embodiment, a customized ophthalmic lens is designed which includes the subjectively optimized values for both low order sphero-cylindrical blur and higher order aberrations such as spherical aberration. The refinement of and improvement in the prescription precision of a proposed final customized ophthalmic lens incorporates one or all of these measurements.

Spherical Aberration affects vision in varying degrees depending on viewing conditions, accommodation, and individual eye characteristics, but it limits the ability of the eye to form a clear image on the retina. Although objective measurements can be made to determine the levels of various aberrations in the eye (including Spherical Aberration), there are other factors in the human visual system that affect what is "seen". Hence, a vision correction approach based purely on objective measurement of the eye's aberrations does not necessarily correspond to better vision.

The apparatus in the present invention incorporates a design which enables the user to vary the amount of spherical aberration introduced into the vision system. The apparatus is depicted in FIG. 1. A subject looks through the apparatus at a visual stimulus and is allowed to adjust the spherical aberration until the best image is perceived. In an alternate embodiment, the user interacts with the examiner to determine the best end point using psychophysical questions. Adjustment of the apparatus is directly analogous to the way that the focus adjust knob on a pair of binoculars allows the user to achieve the best image when looking through its eyepiece. Adjustments on the apparatus are made by turning two micrometers (one for each eye) until the subject perceives best vision.

Figure 2:
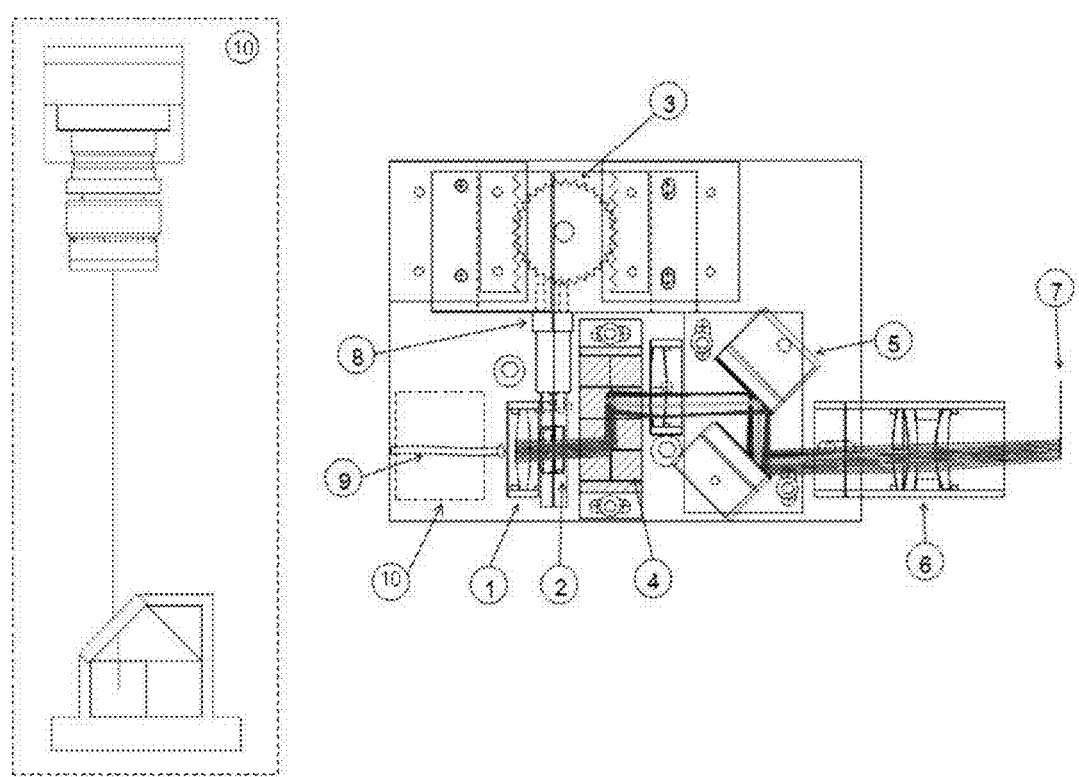
FIG. 2 is a schematic drawing of the device such as that of FIG. 1 that shows optical elements within the apparatus to generate and determine subjective values of higher order aberrations.

Referring to FIG. 2, the optical path for one side or one eye of the apparatus of the invention is shown. The amount of aberration is varied by the mechanical translation of continuously variable aberration generators (2). These generators are transparent phase plates whose presence in an optical path induces spherical aberration. Two phase plates are needed in the path of each eye. By translating the plates laterally with respect to each other, the amount of induced spherical aberration can be adjusted. A suitable telescope arrangement is provided for the subject to view a target at a specified distance. The objective of the telescope (1) is separated from the eyepiece (6) of the telescope.

Aberration induced by the aberration generators (2) is imaged into the pupil of the eye (7). Additional mirrors or prisms (4,5) are required to rotate the image to its original orientation. A person looking through the apparatus will thus see the same scene in front of him or her properly oriented, but with the additional effects of spherical aberration on the image. The subject using the apparatus rotates the micrometer knob (8) to vary the amount of aberration introduced into the system. In an alternate embodiment, this could be an electronic linkage such as a joystick, knob or the like.

The alignment of the apparatus to the subject's eyes is adjusted before each test using manual translation stages (3). During alignment, a video camera on the optics platform is used to increase positioning accuracy, and the eyes are illuminated for the camera by LEDs (9), one LED for each eye. The LEDs emit light in the near infrared region of the spectrum, preferably a center wavelength of approximately 865 nm with a Full Width Half Maximum bandwidth of 90 nm. After alignment, the LEDs (9) are turned off and the camera is removed from the platform. Only standard room lighting and/or controlled illumination of the wall chart or scene are used during the test. In an alternative embodiment, a beam splitter sends (perpendicularly to the optical plane) the image of the pupil to a permanent camera system (10), allowing for constant monitoring of pupil location relative to the optical axis of the system. In this arrangement, the camera output is displayed on a monitor and the examiner adjusts the alignment of the system so that the pupil is centered on the center of the aperture displayed on the monitor, and hence the center of the system. The camera can preferably include a system such as a PixeLink PL-B741EU-R camera with 23 mm EFL color corrected Schneider compact lens attached. It is a 1.3 Mega Pixel, monochrome with IR enhancement, USB connection camera.

Much in the same way that an Eye Care Practitioner uses a patient's subjective responses to generate a standard sphero-cylindrical prescription, the apparatus of the present invention is a tool used to obtain subjective feedback on how aberrations such as spherical aberration affect a person's vision and what level of correction is subjectively preferred. The apparatus of the present invention allows users to view any visual stimulus and adjust the aberration level until the best and most acceptable image is perceived. Subjective measurement of spherical aberration by the apparatus and method of this invention allows for the collective input of the whole visual system (including the brain) to decide what can be considered "best vision".

The methods of the invention may be implemented by recording the data acquired in testing and measurement with the apparatus of the current invention. The recorded data may be provided in any suitable format including written and transcribed or electronically captured. The aberration data thus captured may be converted to a format useful in generating an ophthalmic correction. This correction may included local power profile, phase profile, sag or elevation profile information, and is used to generate the desired ophthalmic correction for a lens or refractive surgical application. Ophthalmic corrections can be made by this method for the improvement of vision.

The methods of the invention can be embodied as computer readable code on a computer readable medium. The computer readable medium is any data storage device that can store data, which thereafter can be read by a computer system. Examples of computer readable medium include read-only memory, random-access memory, CD-ROMs, DVDs, magnetic tape, optical data storage devices. The computer readable medium can also be distributed over network coupled computer systems so that the computer readable code is stored and executed in a distributed fashion.

The invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for example, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

Devices according to the invention may also be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention as set forth in the claims.

User input may be received from the keyboard, mouse, pen, voice, touch screen, or any other means by which a human can input data to a computer, including through other programs such as application programs.

One skilled in the art of computer science will readily be able to combine the software created as described with appropriate general purpose or special purpose computer hardware to create a computer system or computer subsystem embodying the method of the invention.

The methods embodied in, for example, the computer instructions on computer readable media are used to produce the designs described above. The designs created according to one of the methods described above are used to produce lenses. Preferably, the lenses are contact lenses. Illustrative materials for formation of soft contact lenses include, without limitation, silicone elastomers, silicone-containing macromers including, without limitation, those disclosed in U.S. Pat. Nos. 5,371,147, 5,314,960, and 5,057,578 incorporated in their entireties by reference, hydrogels, silicone-containing hydrogels, and the like and combinations thereof. More preferably, the surface is a siloxane, or contains a siloxane functionality including, without limitation, polydimethyl siloxane macromers, methacryloxypropyl siloxanes, and mixtures thereof, silicone hydrogel or a hydrogel. Illustrative materials include, without limitation, aquafilcon, etafilcon, genfilcon, lenefilcon, senefilcon, balafilcon, lotrafilcon, galyfilcon or narafilcon.

Curing of the lens material may be carried out by any convenient method. For example, the material may be deposited within a mold and cured by thermal, irradiation, chemical, electromagnetic radiation curing and the like and combinations thereof. Preferably, molding is carried out using ultraviolet light or using the full spectrum of visible light. More specifically, the precise conditions suitable for curing the lens material will depend on the material selected and the lens to be formed. Suitable processes are disclosed in U.S. Pat. Nos. 4,495,313, 4,680,336, 4,889,664, 5,039,459, and 5,540,410 incorporated herein in their entireties by reference.

The contact lenses of the invention may be formed by any convenient method. One such method uses a lathe to produce mold inserts. The mold inserts in turn are used to form molds. Subsequently, a suitable lens material is placed between the molds followed by compression and curing of the resin to form the lenses of the invention. One ordinarily skilled in the art will recognize that any other number of known methods may be used to produce the lenses of the invention.

EXAMPLES

Example 1

The repeatability of subjective spherical aberration measurements using the inventive apparatus of the present invention was evaluated with 14 study subjects. A total of four measurement sessions with two days between each session were required for each study subject. Subjects were required to be between the ages 18 and 39 and could not have any ocular infection or medication. Since the inventive apparatus as used did not have any power correction devices, the study subjects additionally had to be emmetropic either naturally or by spherical contact lens correction. A Visual Acuity check was administered prior to participation and a score of at least $20/20^{-2}$ in each eye was required to continue the study. All subjects who passed the Visual Acuity screening were also seated in front of a Shack-Hartmann Aberrometer developed and used at the University of Arizona (Jain, 2006) where objective wavefront measurements of each eye were taken. If the subject wore contact lenses, the measurements were taken with the contacts in place. Significant power error or astigmatism were cause for dismissal of one or both eyes from the study.

Figure 3:
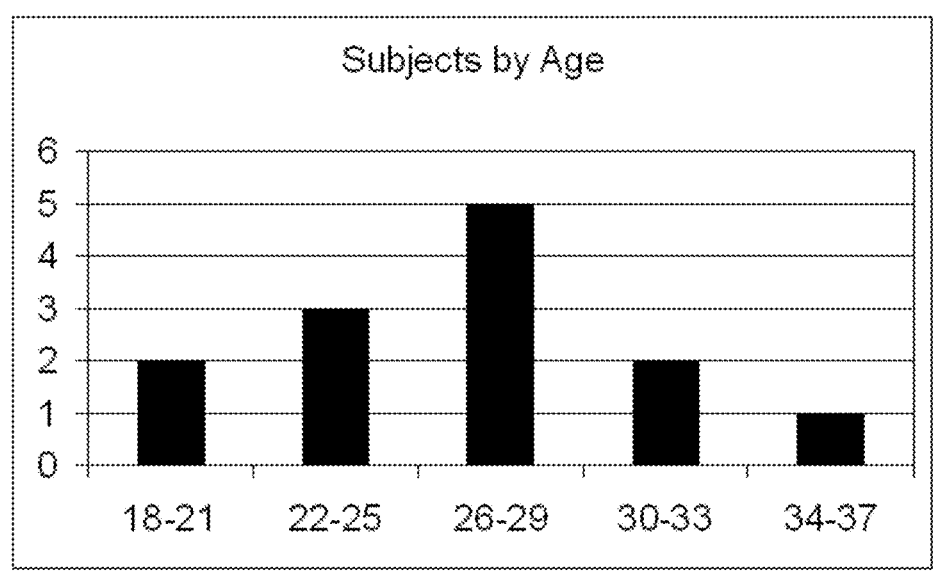
FIG. 3 Is a graphical representation of data that shows the distribution of subjects by age in a clinical study performed with the inventive apparatus.
Figure 5A:
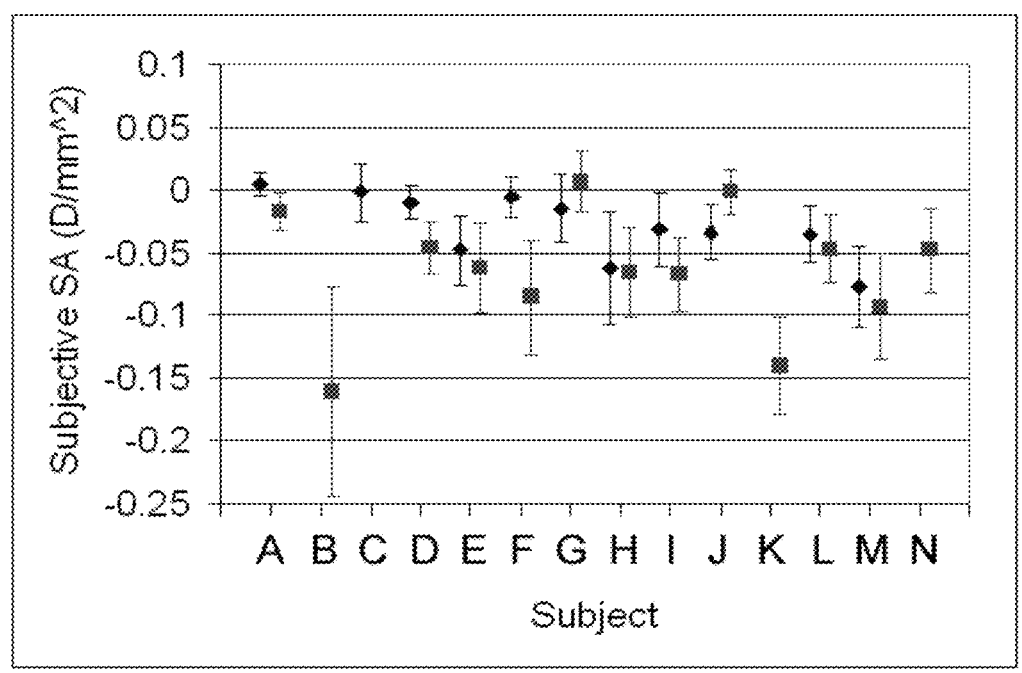
FIG. 5A Is a graphical representation of data that shows subjective spherical aberration measurement results by subject, monocularly with an eye chart.
Figure 5B:
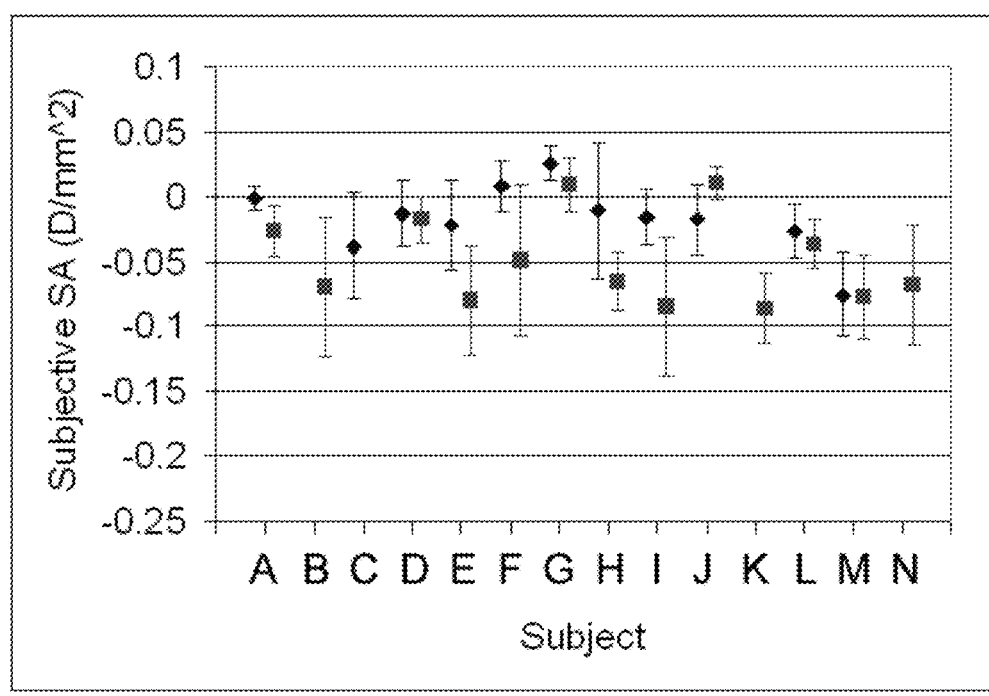
FIG. 5B Is a graphical representation of data that shows subjective spherical aberration measurement results by subject, binocularly with an eye chart.
Figure 5C:
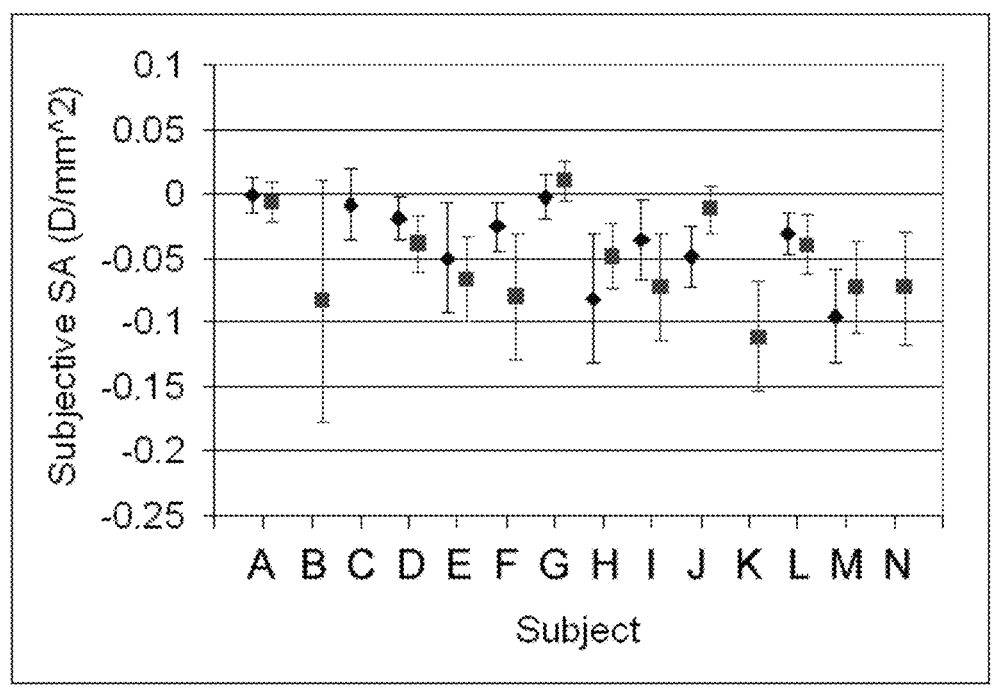
FIG. 5C Is a graphical representation of data that shows subjective spherical aberration measurement results by subject, monocularly with a photo scene.
Figure 5D:
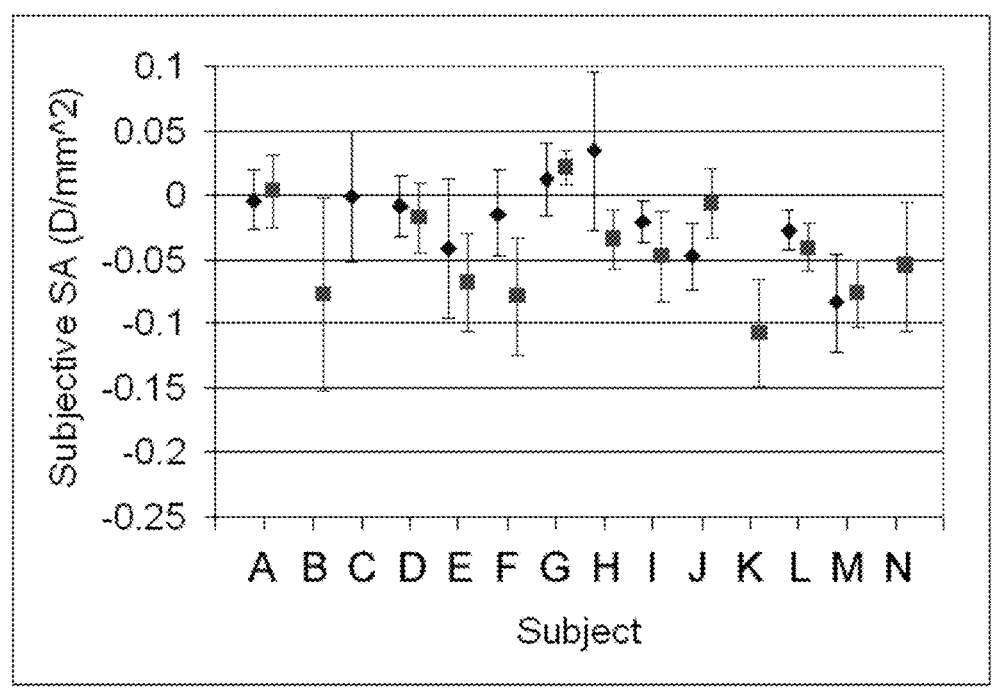
FIG. 5D Is a graphical representation of data that shows subjective spherical aberration measurement results by subject, binocularly with a photo scene.

The distribution of subjects by age is shown in FIG. 3 with the average age being 27 years. By analyzing objective Shack-Hartmann data, the conventional sphere-cylindrical power error and astigmatism for each eye was measured along with the inherent spherical aberration. The subjects each made a total of 24 measurements with the inventive apparatus during each of the four sessions. Two vision targets were used: an ETDRS eye chart (FIG. 4) and a real world photo scene. The two kinds of targets provided a variety of spatial frequencies and contrast levels and were alternated randomly at 20 feet from the subject. Three measurement iterations were made for each vision target and both binocular and monocular measurements were made for each iteration. For each measurement session, the subject's task was to adjust the spherical aberration until the image seen through the inventive apparatus was subjectively perceived as the best image. If the range of acceptable adjustments was wide, the subject was instructed to find the midpoint between two positions at which the image degradation was noticeable. The order of the measurements was randomized within a session, but the same 24 measurements were made in every session. The subjects completed the four sessions over a period of between 7 to 15 days at various times of the day.

Four measurement conditions were used for each eye: monocular with eye chart, binocular with eye chart, monocular with photo scene, and binocular with photo scene. Each condition had three measurements per session. The average and standard deviation of the 12 measurements for each condition and each eye were calculated. Any data points beyond 2 standard deviations of the average were removed and the average and standard deviation were recalculated for this reduced data set. On average 11 or all 12 of the data points were used. The results of the subjective measurements are shown by subject in FIGS. 5A, 5B, 5C and 5D. In the FIG. 5, data obtained with left eyes are denoted by diamonds and data from right eyes are denoted by squares.

A summary of the measurement values for each of the four conditions is given in Table 1. The standard deviation values represent the repeatability of the device as used. Table 1 indicates that the average user will choose a subjective spherical aberration correction repeatably to within 0.03 $D/mm^2$. For the subjects tested, the average repeatability across the four conditions is 0.031 $D/mm^2$, with a standard deviation of 0.015 $D/mm^2$. Some subjects showed large deviations, particularly noticeable in the data from subject B.

TABLE 1

| Condition | Mean Average Subjective SA ($D/mm^2$) | Mean Std. Deviation ($D/mm^2$) | Maximum Average Value ($D/mm^2$) | Minimum Average Value ($D/mm^2$) |
|---|---|---|---|---|
| Monocular Eye Chart | −0.048 | 0.030 | 0.007 | −0.161 |
| Binocular Eye Chart | −0.035 | 0.030 | 0.026 | −0.086 |
| Monocular Photo Scene | −0.046 | 0.031 | 0.010 | −0.111 |
| Binocular Photo Scene | −0.033 | 0.034 | 0.034 | −0.107 |

Figure 6:
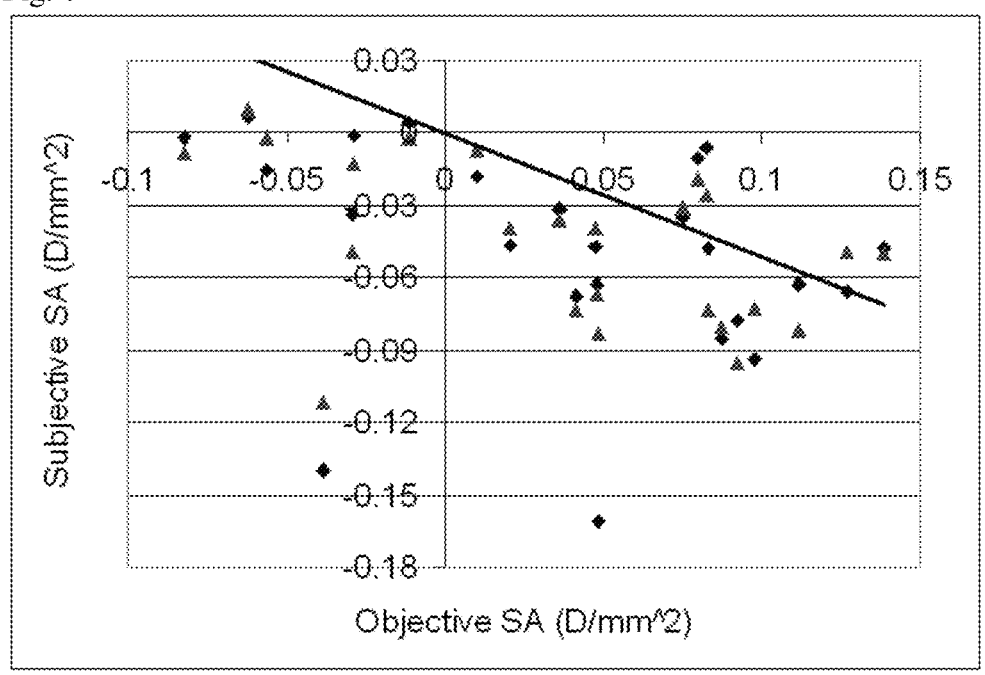
FIG. 6 Shows a plot of subjective spherical aberration as a function of objective spherical aberration measurements.

FIG. 6 shows the plotted subjective aberration values as a function of objective aberration measurements for both the monocular eye chart and monocular photo scene conditions for all 24 eyes. A linear regression fit indicates very little correlation between the two measurements. Diamonds represent data obtained with the eye chart and triangles represent the data obtained with the photo scene. The regression line has a slope of −0.5 and has been forced to pass through the origin.

Figure 7:
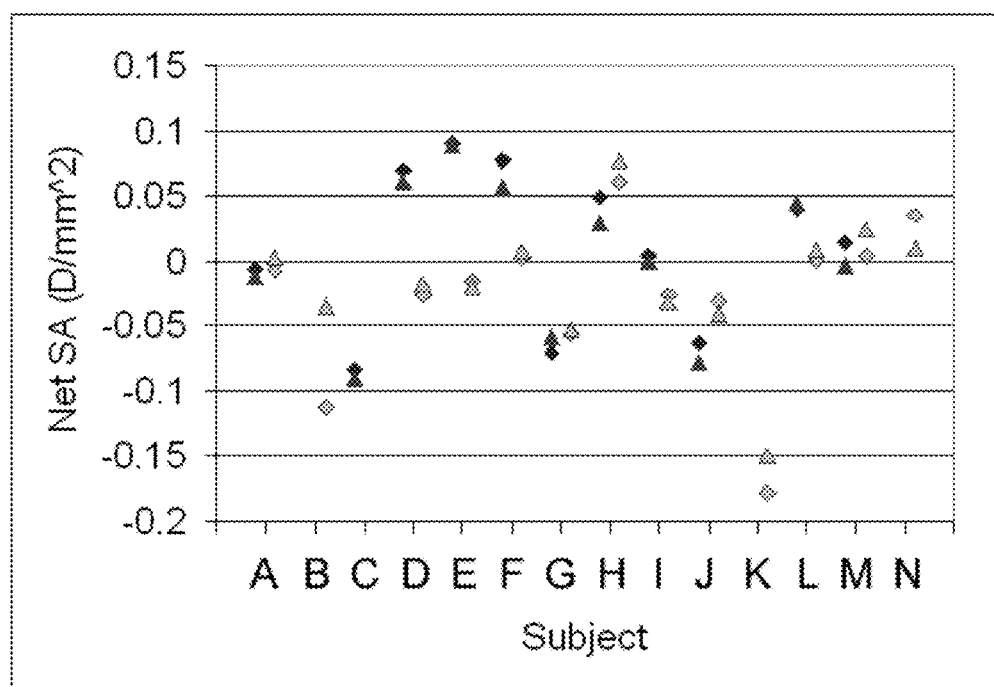
FIG. 7 Is a graphical representation of data that shows the net difference spherical aberration values by subject.

The measurements from the inventive apparatus and the Shack-Hartmann wavefront sensor can be used to determine the net desired Spherical Aberration for a given eye. FIG. 7 shows the calculated net Spherical Aberration values for each subject. Diamonds represent eye chart data and triangles represent photo scene data. Left eye data are darker than the right eye data. Inspection of FIG. 7 clearly indicates that there is a fundamental difference between the objective measurement and the subjective measurement of spherical aberration. Here it is clear that the general net or difference in spherical aberration is not only non-zero, but is greatly different from subject to subject.

In the alternative embodiment of the device where a permanent camera system 10 is employed, the variability in the subjective measurements can be reduced. The evaluation of the variability in measurement of subjective spherical aberration was undertaken in a study with two subjects, average age of 35 years. The subjects had no ocular infection or medication, and were naturally emmetropic (no habitual vision correction). Objective Shack-Hartmann data was obtained for each subject, and the conventional sphere-cylindrical power error and astigmatism was measured along with the inherent spherical aberration. The subject viewed the same visual stimulus (real world digital photographic scene presented on a digital monitor), both during the measurement using the objective Shack-Hartmann aberrometer, and during measurement with the inventive apparatus.

Measurements were performed with the inventive device with and without the camera alignment system in place. The measurements were taken over separate sessions, over multiple days, and three subjective measurements of spherical aberration were recorded during each session.

A summary of the measurement values for each subject given in Table 2. The standard deviation values represent the repeatability of the device as used, and it is demonstrated that the standard deviation is significantly reduced with the introduction of the camera alignment system.

TABLE 2

| Condition | Subject 1: Mean Average Subjective SA (D/mm$^2$) | Subject 1: Mean Std. Deviation (D/mm$^2$) | Subject 2: Mean Average Subjective SA (D/mm$^2$) | Subject 2: Mean Std. Deviation (D/mm$^2$) |
|---|---|---|---|---|
| Without camera alignment feedback | −0.046 | 0.039 | *** | *** |
| With camera alignment feedback | −0.044 | 0.014 | −0.087 | 0.026 |

Figure 8A:
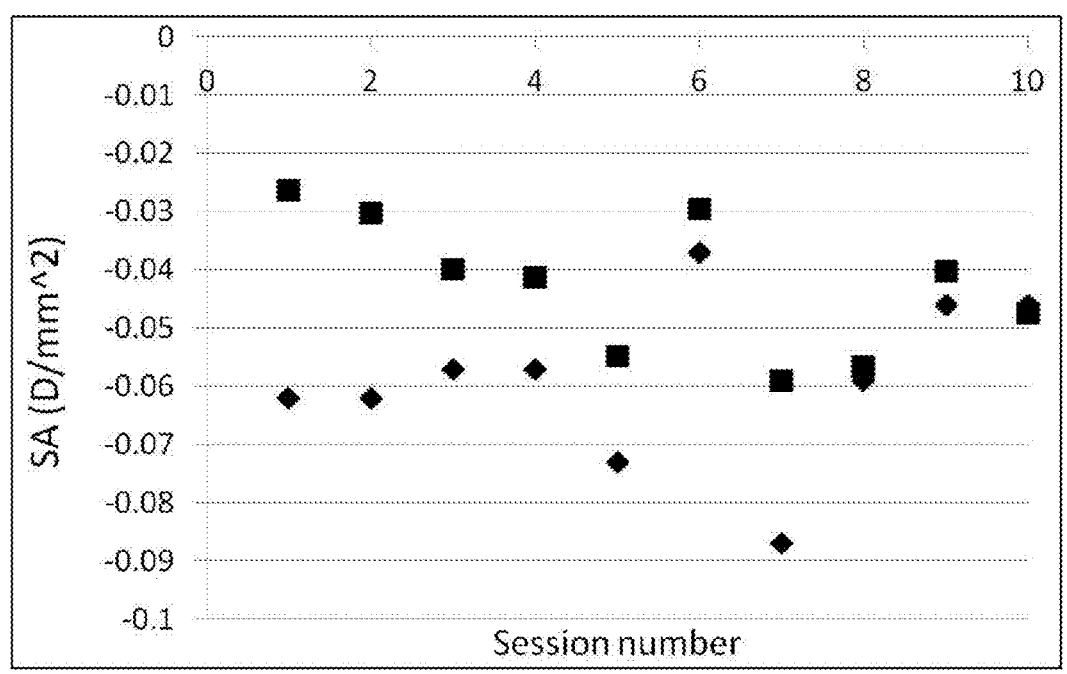
FIG. 8A Shows a plot of subjective spherical aberration and objective spherical aberration measurements for a first subject.
Figure 8B:
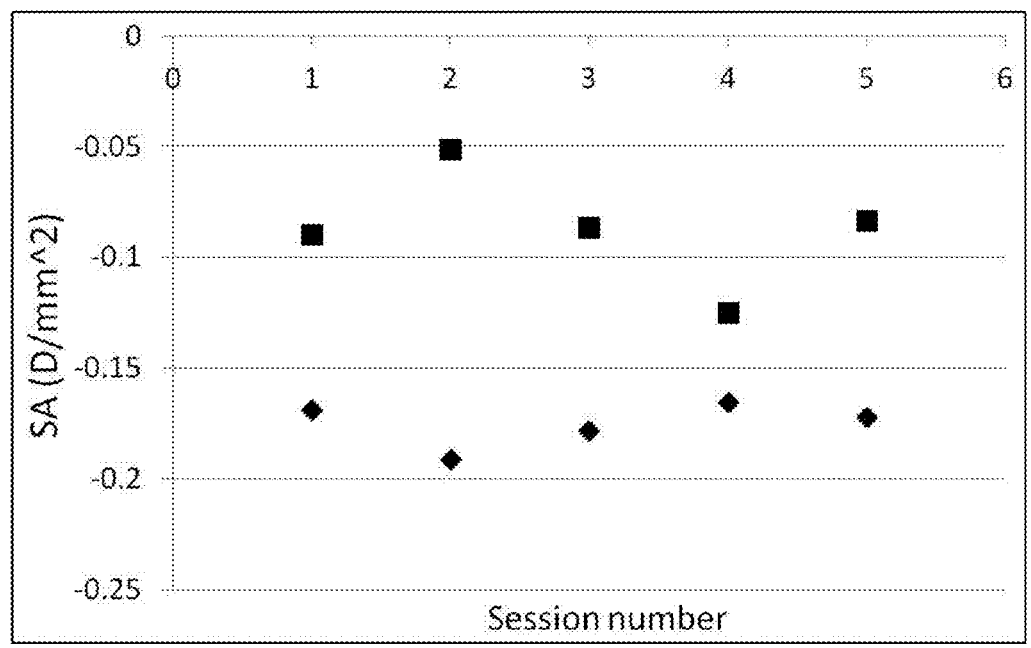
FIG. 8B Shows a plot of subjective spherical aberration and objective spherical aberration measurements for a second subject.

FIGS. 8A and 8B show the spherical aberration measurements obtained for the two subjects, both with the inventive device, as well as with an objective aberration measurement system (Shack-Hartmann COAS aberrometer). Squares represent data obtained with the inventive device, and diamonds represent data obtained objective Shack-Hartmann aberrometer. In this case, as in the previous example, inspection of FIGS. 8A and 8B clearly indicates a difference between the objective measurement with the aberrometer, and the subjective measurement of spherical aberration with the inventive device. Here it is also clear that the subjectively preferred spherical aberration is not zero. In addition, we can clearly see that the subjective spherical aberration is consistently lower than that obtained from the objectively measured values. It is also clear in this as well as the previous example that spherical aberration is different from subject to subject.

We claim:

1. A method of providing an ophthalmic correction comprising:
   a. obtaining low order subjective sphero-cylindrical refractive patient data;
   b. obtaining the subjective measurement of visual aberrations of a subject's eye, comprising an adjustable, aberration-generating optical assembly that introduces controlled levels of aberrations onto the pupil plane of a test subject's eye, the optical assembly including a pair of mating polynomial plates, placed in the visual path, which introduces specific controlled amounts of aberrations into the ocular wavefront when shifted laterally by a calibrated amount, a 1X Keplerian telescope, the telescope having a real exit pupil external to the telescope, so that efficient coupling is achieved between the pupil of the eye and the aberrations introduced by the generator and an adjustment device configured to adjust the aberration until the best image is perceived by the subject; and
   c. generating an ophthalmic correction which incorporates these measurements.

* * * * *